US012569460B2

(12) United States Patent
Yuan

(10) Patent No.: US 12,569,460 B2
(45) Date of Patent: Mar. 10, 2026

(54) APPLICATION OF THYROID HORMONES AND THYROID HORMONE ANALOGUES TO PREPARATION OF DRUGS FOR TREATING SICKLE-CELL DISEASE

(71) Applicant: RUIJIN HOSPITAL, SHANGHAI JIAO TONG UNIVERSITY SCHOOL OF MEDICINE, Shanghai (CN)

(72) Inventor: Hao Yuan, Shanghai (CN)

(73) Assignee: RUIJIN HOSPITAL, SHANGHAI JIAO TONG UNIVERSITY SCHOOL OF MEDICINE, Shanghai (CN)

( * ) Notice: Subject to any disclaimer, the term of this patent is extended or adjusted under 35 U.S.C. 154(b) by 683 days.

(21) Appl. No.: 18/046,513

(22) Filed: Oct. 14, 2022

(65) Prior Publication Data

US 2023/0190691 A1     Jun. 22, 2023

Related U.S. Application Data

(63) Continuation of application No. PCT/CN2021/072734, filed on Jan. 19, 2021.

(30) Foreign Application Priority Data

Apr. 17, 2020     (CN) .......................... 202010304072.0

(51) Int. Cl.
*A61K 31/198* (2006.01)
*A61K 31/192* (2006.01)
*A61P 7/06* (2006.01)

(52) U.S. Cl.
CPC .......... *A61K 31/198* (2013.01); *A61K 31/192* (2013.01); *A61P 7/06* (2018.01)

(58) Field of Classification Search
CPC ........ A61K 31/198; A61K 31/192; A61P 7/06
See application file for complete search history.

(56) References Cited

FOREIGN PATENT DOCUMENTS

CN     111419834     7/2020

OTHER PUBLICATIONS

Ebert et al., High Throughput Screen to Identify Small Molecules That Differentially Regulate Expression of the Globin Genes., Blood, 2005, 106(11): 3632 (Year: 2005).*

(Continued)

*Primary Examiner* — Savitha M Rao
*Assistant Examiner* — Andrew P Lee
(74) *Attorney, Agent, or Firm* — JCIPRNET

(57) ABSTRACT

The present invention provides an application of thyroid hormones and thyroid hormone analogues to preparation of drugs for treating sickle-cell disease, particularly an application to preparation of drugs for improving the expression quantity of $\zeta$-globin. During the differentiation of K562 cells, thyroid hormone analogue (Triac) can significantly up-regulate the expression of $\zeta$globin gene (HBZ) by 50 folds or above. The expression of $\zeta$-globin gene (hbae5) can also be up-regulated by 30-70 folds in zebrafish treated with thyroid hormones and thyroid hormone analogues. Therefore, according to the present invention, the expression of $\zeta$-globin gene can be significantly activated by thyroid hormones and thyroid hormone analogues which may develop new potential therapies for patients with sickle-cell disease. It provides an economical, safe and effective method for treating sickle-cell disease and can be widely used.

1 Claim, 2 Drawing Sheets

Specification includes a Sequence Listing.

(56)                     References Cited

OTHER PUBLICATIONS

Sherman et al., Augmented Hepatic and Skeletal Thyromimetic Effects of Tiratricol in Comparison with Levothyroxine, Journal of Clinical Endocrinology and Metabolism, 1997, 82(7), pp. 2153-2158 (Year: 1997).*

"International Search Report (Form PCT/ISA/210) of PCT/CN2021/072734", mailed on Apr. 16, 2021, with English translation thereof, pp. 1-10.

"Written Opinion of the International Searching Authority (Form PCT/ISA/237) of PCT/CN2021/072734," mailed on Apr. 16, 2021, pp. 1-6.

J. E. Fuhr et al., "Control of Hemoglobin Synthesis in Fetal Erythroid Cells by L-Thyroxine," American Journal of Hematology, vol. 5, Dec. 1978, pp. 163-168.

J. E. Fuhr et al., "In Vitro Stimulation of Primate Hemoglobin Synthesis by L-Thyroxine," Blood, vol. 49, Mar. 1977, pp. 407-413.

Nurdan Evliyaoğlu et al., "Thyroid functions in mild and severe forms of sickle cell anemia," Acta Paediatrica Japonica, vol. 38, Apr. 1996, pp. 460-463.

Ashraf T Soliman et al., "Chronic anemia and thyroid function," Acta Biomed., vol. 88, Dec. 2017, pp. 119-127.

* cited by examiner

SEQUENCE LISTING

```
Sequence total quantity: 30
SEQ ID NO: 1            moltype = DNA   length = 429
FEATURE                 Location/Qualifiers
misc_feature            1..429
                        note = Human -globin gene sequence
source                  1..429
                        mol_type = other DNA
                        organism = synthetic construct
SEQUENCE: 1
atgtctctga ccaagactga gaggaccatc attgtgtcca tgtgggccaa gatctccacg   60
caggccgaca ccatcggcac cgagactctg gagaggctct tcctcagcca cccgcagacc  120
aagacctact tcccgcactt cgacctgcac ccggggtccg cgcagttgcg cgcgcacggc  180
tccaaggtgg tggccgccgt gggcgacgcg gtgaagagca tcgacgacat cggcggcgcc  240
ctgtccaagc tgagcgagct gcacgcctac atcctgcgcg tggacccggt caacttcaag  300
ctcctgtccc actgcctgct ggtcaccctg gccgcgcgct tccccgccga cttcacggcc  360
gaggcccacg ccgcctggga caagttccta tcggtcgtat cctctgtcct gaccgagaag  420
taccgctga                                                         429

SEQ ID NO: 2            moltype = DNA   length = 18
FEATURE                 Location/Qualifiers
misc_feature            1..18
                        note = Human--actin-F
source                  1..18
                        mol_type = other DNA
                        organism = synthetic construct
SEQUENCE: 2
ccaaccgcga gaagatga                                                 18

SEQ ID NO: 3            moltype = DNA   length = 20
FEATURE                 Location/Qualifiers
misc_feature            1..20
                        note = Human--actin-R
source                  1..20
                        mol_type = other DNA
                        organism = synthetic construct
SEQUENCE: 3
ccagaggcgt acagggatag                                               20

SEQ ID NO: 4            moltype = DNA   length = 17
FEATURE                 Location/Qualifiers
misc_feature            1..17
                        note = Human-HBA1/2-F
source                  1..17
                        mol_type = other DNA
                        organism = synthetic construct
SEQUENCE: 4
aaggtcggcg cgcacgc                                                  17

SEQ ID NO: 5            moltype = DNA   length = 18
FEATURE                 Location/Qualifiers
misc_feature            1..18
```

-continued

```
                              note = Human-HBA1/2-R
source                        1..18
                              mol_type = other DNA
                              organism = synthetic construct
SEQUENCE: 5
ctcaggtcga agtgcggg                                                18

SEQ ID NO: 6             moltype = DNA   length = 21
FEATURE                  Location/Qualifiers
misc_feature             1..21
                              note = Human-HBZ-F
source                   1..21
                              mol_type = other DNA
                              organism = synthetic construct
SEQUENCE: 6
ggaccatcat tgtgtccatg t                                            21

SEQ ID NO: 7             moltype = DNA   length = 21
FEATURE                  Location/Qualifiers
misc_feature             1..21
                              note = Human-HBZ-R
source                   1..21
                              mol_type = other DNA
                              organism = synthetic construct
SEQUENCE: 7
gggaagtagg tcttggtctg c                                            21

SEQ ID NO: 8             moltype = DNA   length = 20
FEATURE                  Location/Qualifiers
misc_feature             1..20
                              note = Human-HBE1-F
source                   1..20
                              mol_type = other DNA
                              organism = synthetic construct
SEQUENCE: 8
tgcatgtgga tcctgagaac                                              20

SEQ ID NO: 9             moltype = DNA   length = 19
FEATURE                  Location/Qualifiers
misc_feature             1..19
                              note = Human-HBE1-R
source                   1..19
                              mol_type = other DNA
                              organism = synthetic construct
SEQUENCE: 9
cgacagcaga caccagctt                                               19

SEQ ID NO: 10            moltype = DNA   length = 20
FEATURE                  Location/Qualifiers
misc_feature             1..20
                              note = Human-HBG1/2-F
source                   1..20
                              mol_type = other DNA
                              organism = synthetic construct
SEQUENCE: 10
agcacctgga tgatctcaag                                              20

SEQ ID NO: 11            moltype = DNA   length = 20
FEATURE                  Location/Qualifiers
misc_feature             1..20
                              note = Human-HBG1/2-R
source                   1..20
                              mol_type = other DNA
                              organism = synthetic construct
SEQUENCE: 11
aaacggtcac cagcacattt                                              20

SEQ ID NO: 12            moltype = DNA   length = 19
FEATURE                  Location/Qualifiers
misc_feature             1..19
                              note = Human-HBD-F
source                   1..19
                              mol_type = other DNA
                              organism = synthetic construct
SEQUENCE: 12
gatgcagttg gtggtgagg                                               19

SEQ ID NO: 13            moltype = DNA   length = 19
FEATURE                  Location/Qualifiers
```

-continued

```
misc_feature            1..19
                        note = Human-HBD-R
source                  1..19
                        mol_type = other DNA
                        organism = synthetic construct
SEQUENCE: 13
gggttgccca taacagcat                                                           19

SEQ ID NO: 14           moltype = DNA  length = 20
FEATURE                 Location/Qualifiers
misc_feature            1..20
                        note = Human-HBB-F
source                  1..20
                        mol_type = other DNA
                        organism = synthetic construct
SEQUENCE: 14
gcacgtggat cctgagaact                                                          20

SEQ ID NO: 15           moltype = DNA  length = 20
FEATURE                 Location/Qualifiers
misc_feature            1..20
                        note = Human-HBB-R
source                  1..20
                        mol_type = other DNA
                        organism = synthetic construct
SEQUENCE: 15
cactggtggg gtgaattctt                                                          20

SEQ ID NO: 16           moltype = DNA  length = 432
FEATURE                 Location/Qualifiers
misc_feature            1..432
                        note = Zebrafish -globin gene sequence
source                  1..432
                        mol_type = other DNA
                        organism = synthetic construct
SEQUENCE: 16
atgagtcttt ctgctaaaga caaggccgcc gtgaggggct tctgggccaa gattgcccca    60
aagggagagc aaattggtaa cgaggcgttt tccagattgc ttttggtgta ccctcagacc   120
aagacctact tctcccactg gaacgatctg gcccccggct ctccctctgt gaagaagcag   180
ggaaagaaga tcgtcggtgg actcggtctg gctgttgata aaatcgacga ccttttcaac   240
ggcctgctga acctcagtga attgcacgcc tttcagctga gagtcgaccc tgctaacttc   300
aagctcctgt ctcactgtct gctggtggtg ttcgccatgc tcttccctga tgacttcacc   360
gctgaggtcc atctggccat cgacaagttc ctggcaagag tggctttggc tctgtctgac   420
aaatatcgtt aa                                                        432

SEQ ID NO: 17           moltype = DNA  length = 20
FEATURE                 Location/Qualifiers
misc_feature            1..20
                        note = Zebrafish--actin-F
source                  1..20
                        mol_type = other DNA
                        organism = synthetic construct
SEQUENCE: 17
tgctgttttc ccctccattg                                                          20

SEQ ID NO: 18           moltype = DNA  length = 19
FEATURE                 Location/Qualifiers
misc_feature            1..19
                        note = Zebrafish--actin-R
source                  1..19
                        mol_type = other DNA
                        organism = synthetic construct
SEQUENCE: 18
ttctgtccca tgccaacca                                                           19

SEQ ID NO: 19           moltype = DNA  length = 21
FEATURE                 Location/Qualifiers
misc_feature            1..21
                        note = Zebrafish-hbae1-F
source                  1..21
                        mol_type = other DNA
                        organism = synthetic construct
SEQUENCE: 19
ctgaggctgt cagcaaaatc g                                                        21

SEQ ID NO: 20           moltype = DNA  length = 21
FEATURE                 Location/Qualifiers
misc_feature            1..21
                        note = Zebrafish-hbae1-R
```

-continued

```
source                       1..21
                             mol_type = other DNA
                             organism = synthetic construct
SEQUENCE: 20
gaacaaagtg gccagaacca c                                          21

SEQ ID NO: 21               moltype = DNA  length = 21
FEATURE                     Location/Qualifiers
misc_feature                1..21
                            note = Zebrafish-hbae3-F
source                      1..21
                            mol_type = other DNA
                            organism = synthetic construct
SEQUENCE: 21
gctgatggat gacctgaagg g                                          21

SEQ ID NO: 22               moltype = DNA  length = 21
FEATURE                     Location/Qualifiers
misc_feature                1..21
                            note = Zebrafish-hbae3-R
source                      1..21
                            mol_type = other DNA
                            organism = synthetic construct
SEQUENCE: 22
ctcaggagtg aagtcgtctg g                                          21

SEQ ID NO: 23               moltype = DNA  length = 21
FEATURE                     Location/Qualifiers
misc_feature                1..21
                            note = Zebrafish-hbae5-F
source                      1..21
                            mol_type = other DNA
                            organism = synthetic construct
SEQUENCE: 23
tgctgaacct cagtgaattg c                                          21

SEQ ID NO: 24               moltype = DNA  length = 21
FEATURE                     Location/Qualifiers
misc_feature                1..21
                            note = Zebrafish-hbae5-R
source                      1..21
                            mol_type = other DNA
                            organism = synthetic construct
SEQUENCE: 24
ggaacttgtc gatggccaga t                                          21

SEQ ID NO: 25               moltype = DNA  length = 20
FEATURE                     Location/Qualifiers
misc_feature                1..20
                            note = Zebrafish-hbbe1-F
source                      1..20
                            mol_type = other DNA
                            organism = synthetic construct
SEQUENCE: 25
tccacgtaga tcccgacaac                                            20

SEQ ID NO: 26               moltype = DNA  length = 20
FEATURE                     Location/Qualifiers
misc_feature                1..20
                            note = Zebrafish-hbbe1-R
source                      1..20
                            mol_type = other DNA
                            organism = synthetic construct
SEQUENCE: 26
tactgtcttc ccagagcgga                                            20

SEQ ID NO: 27               moltype = DNA  length = 21
FEATURE                     Location/Qualifiers
misc_feature                1..21
                            note = Zebrafish-hbbe2-F
source                      1..21
                            mol_type = other DNA
                            organism = synthetic construct
SEQUENCE: 27
ggactggaca gagccatgaa g                                          21

SEQ ID NO: 28               moltype = DNA  length = 21
FEATURE                     Location/Qualifiers
misc_feature                1..21
```

-continued

```
                            note = Zebrafish-hbbe2-R
source                      1..21
                            mol_type = other DNA
                            organism = synthetic construct
SEQUENCE: 28
gaggcaatca cgattgtcag g                                        21

SEQ ID NO: 29               moltype = DNA  length = 20
FEATURE                     Location/Qualifiers
misc_feature                1..20
                            note = Zebrafish-hbbe3-F
source                      1..20
                            mol_type = other DNA
                            organism = synthetic construct
SEQUENCE: 29
ttgtgtggac agctgaggag                                          20

SEQ ID NO: 30               moltype = DNA  length = 20
FEATURE                     Location/Qualifiers
misc_feature                1..20
                            note = Zebrafish-hbbe3-R
source                      1..20
                            mol_type = other DNA
                            organism = synthetic construct
SEQUENCE: 30
acggatagac gaccaagcat                                          20
```

APPLICATION OF THYROID HORMONES AND THYROID HORMONE ANALOGUES TO PREPARATION OF DRUGS FOR TREATING SICKLE-CELL DISEASE

CROSS-REFERENCE TO RELATED APPLICATIONS

This application is a continuation of international PCT application serial no. PCT/CN2021/072734, filed on Jan. 19, 2021, which claims the priority benefit of China application serial no. 202010304072.0, filed on Apr. 17, 2020. The entirety of each of the above-mentioned patent applications is hereby incorporated by reference herein and made a part of this specification.

REFERENCE TO A SEQUENCE LISTING

The instant application contains a Sequencing Listing which has been submitted electronically in XML file and is hereby incorporated by reference in its entirety. Said XML copy, created on Sep. 28, 2022, is named 126030-0C_sequencing-listing and is 39,914 bytes in size.

BACKGROUND OF THE INVENTION

1. Technical Field

The present invention belongs to the technical field of sickle-cell disease, and particularly relates to an application of thyroid hormones and thyroid hormone analogues to preparation of drugs for treating sickle-cell disease.

2. Description of Related Art

Sickle-cell disease (SCD) is one of the most common severe monogenic disorders in the world. Estimates suggest that every year approximately 300,000 infants are born with SCD, and that this number could rise to 400,000 by 2050. SCD is a multisystem disease, associated with episodes of acute illness and progressive organ damage. It is caused by a mutation in the 3-globin gene in which the 17th nucleotide is changed from thymine to adenine and the sixth amino acid in the β-globin chain becomes valine instead of glutamic acid ($\beta^{E6V}$). The mutated, assembled hemoglobin, HbS ($\alpha_2\beta^s_2$), undergoes polymerization upon deoxygenation, resulting in erythrocyte deformation, hemolysis, and morbid complications secondary to microvascular occlusion. Although blood transfusion, hydroxyurea, and allogeneic hematopoietic stem cell transplantation can improve survival and quality of life, most patients with SCD have many unmet medical needs, and life expectancy for patients is still reduced by approximately 30 years.

1. The disadvantages of allogeneic hematopoietic stem cell transplantation are:
   Allogeneic hematopoietic stem cell transplantation is limited because of graft versus host disease, engraftment failure, high cost of performing the procedure, limited donor availability and morbidity.
2. The disadvantages of blood transfusion are:
   1) blood transfusion will lead to iron overload to damage multiple organs, mainly affecting heart, liver, pancreas and various endocrine organs;
   2) blood transfusion will cause fever, chills, rash and other adverse effects, and will lead to acute hemolysis, tracheal contraction and blood pressure drop in severe cases;

3) blood transfusion may pose a risk of infectious diseases through blood; and
   4) blood transfusion has high cost, which will cause an economic burden especially for patients who need lifelong blood transfusion.
3. The disadvantages of drug treatment are:
   1) a drug that induces HbF synthesis: hydroxyurea is the first drug approved by FDA to treat SCD. The drug can induce the expression of fetal hemoglobin F (HbF, $\alpha_2\gamma_2$) and alleviate symptoms of patients with SCD. However, hydroxyurea is a cytotoxic agent which inhibits DNA synthesis and repair.
   2) A drug that inhibits HbS polymerization: On Nov. 25, 2019, the FDA granted accelerated approval to voxelotor (Oxbryta, Global Blood Therapeutics) for adults and pediatric patients 12 years of age and older with sickle cell disease. Voxelotor is a hemoglobin modulator that prevents polymerization by increasing the affinity of hemoglobin with oxygen. However, the drug was approved through the accelerated approval pathway, and it remains to be seen whether it will improve the life quality of patients in larger clinical trials. Although the current data shows that Voxelotor is well tolerated, its tolerance in a larger population remains to be observed. Moreover, two patients who used Voxelotor at the same time died, although it was allegedly unrelated to Voxelotor. In addition, the drug is expensive, which brings a huge economic burden to patients.
   ζ-globin (the embryonic form of α-globin) gene expression is normally limited to the early stages of primitive erythropoiesis and transcriptionally silenced at 6 to 7 weeks of gestation. Previous studies showed that in a mouse SCD model, continued expression of the ζ-globin could efficiently inhibit sickle hemoglobin polymerization and alleviate the symptoms of SCD mice without significant negative effects upon oxygen transportation. Hence, Reactivation of the ζ-globin gene will be a new effective method for treating SCD. However, pharmacologic compounds capable of activating ζ-globin gene expression have not yet been available so far.

Therefore, it is urgent to find new types of agents that can induce the expression of the ζ-globin gene.

BRIEF SUMMARY OF THE INVENTION

In view of the above technical problems, the primary objective of the present invention is to provide an application of thyroid hormones and thyroid hormone analogues to preparation of drugs for treating sickle-cell disease.

The second objective of the present invention is to provide an application of thyroid hormones and thyroid hormone analogues to preparation of drugs for increasing the expression of ζ-globin.

To achieve the primary objective, the present invention adopts the following technical solution:

thyroid hormones and thyroid hormone analogues may be applied to preparation of drugs for treating sickle-cell disease.

To achieve the second objective, the present invention adopts the following technical solution:

thyroid hormones and thyroid hormone analogues may be applied to preparation of drugs for regulating the expression of ζ-globin gene.

Specifically, thyroid hormones and thyroid hormone analogues can significantly up-regulate the expression of ζ-globin gene.

Triac (also referred to as Tiratricol or 3,3',5-triiodothyroacetic acid) (chemical name: 2-[4-(4-Hydroxy-3-iodophenoxy)-3,5-diiodophenyl] acetic acid, molecular formula: $C_{14}H_9I_3O_4$) is a thyroid hormone analogue for treating patients with thyroid hormone resistance. In addition, Triac has also displayed therapeutic potential for the treatment of Allan-Herndon-Dudley syndrome.

The inventor found that during the differentiation of K562 cells, Triac could significantly up-regulate the expression of ζ-globin gene (HBZ). Furthermore, Triac could also dramatically induce ζ-globin gene (hbae5) expression in zebrafish. In addition, the inventor also found that thyroid hormones (3,3',5-Triiodo-L-thyronine, T3 for short or 3,3', 5,5'-tetraiodothyronine, T4 for short) had a similar effect. Therefore, the inventor discovered for the first time that the thyroid hormone analogue (Triac) and thyroid hormones (T3 or T4) could significantly induce ζ-globin gene expression both in vitro and in vivo, which may allow development of new therapies for sickle-cell disease.

Specifically, Triac was purchased from USA Selleck Biotechnology Co., Ltd., T3 (3,3',5-Triiodo-L-thyronine) was purchased from Sigma Company, and T4 (3,3',5,5'-tetraiodothyronine) was purchased from Biological Engineering (Shanghai) Ltd., Co.

Due to the above solutions, the present invention has the following beneficial effects:

according to the present invention, thyroid hormones (T3 and T4) and thyroid hormone analogue (Triac) act as a potent inducer of ζ-globin expression, which may sever as a new potential therapeutic option for patients with sickle-cell disease. It provides an economical, safe and effective method for the treatment of sickle-cell disease and can be widely used.

DETAILED DESCRIPTION OF THE INVENTION

The present invention provides application of thyroid hormones and thyroid hormone analogues to preparation of drugs for treating sickle-cell disease.

Experimental Materials:

K562 cells were cultured in RPMI 1640 medium supplemented with 10% (v/v) fetal bovine serum; Hemin was dissolved into 0.2 mol/L NaOH solution, and the working concentration for treating K562 cells is 20 μmol/L; Triac, T3 and T4 were dissolved into dimethyl sulfoxide (DMSO), and the working concentration for treating K562 cells and zebrafish embryos is 20 μmol/L and 5 μmol/L, respectively.

The present invention is further described below with reference to embodiments.

Embodiment 1

In K562 cells, the process that Triac significantly activates the expression of ζ-globin gene (HBZ) is:

K562 cells were treated with hemin or hemin plus Triac for 72 hours, respectively, centrifugation was performed at 2000 rpm for 5 minutes to collect cells, a TRIzol reagent (Invitrogen) was used to extract total RNA, then a reverse transcription kit (ReverTra Ace, TOYOBO) was used to synthesize cDNA, and finally, a SYBR Green Realtime PCR Master Mix (TOYOBO) reagent was used to perform quantitative PCR.

The quantitative PCR reaction system is:

| | |
|---|---|
| 2 × SYBR Green PCR Master Mix | 5 ul |
| F-Primer(10 μmol/L) | 0.6 ul |
| R-Primer(10 μmol/L) | 0.6 ul |
| cDNA | 1 ul |
| ddH2O | 2.8 ul |
| Total volume | 10 ul |

The quantitative PCR reaction conditions are:

hot start: 95° C., 10 minutes;

denaturation: 95° C., 10 seconds; and annealing/extension: 60° C., 30 seconds.

40 circles.

Analysis of a Solubility Curve

Figure 1:
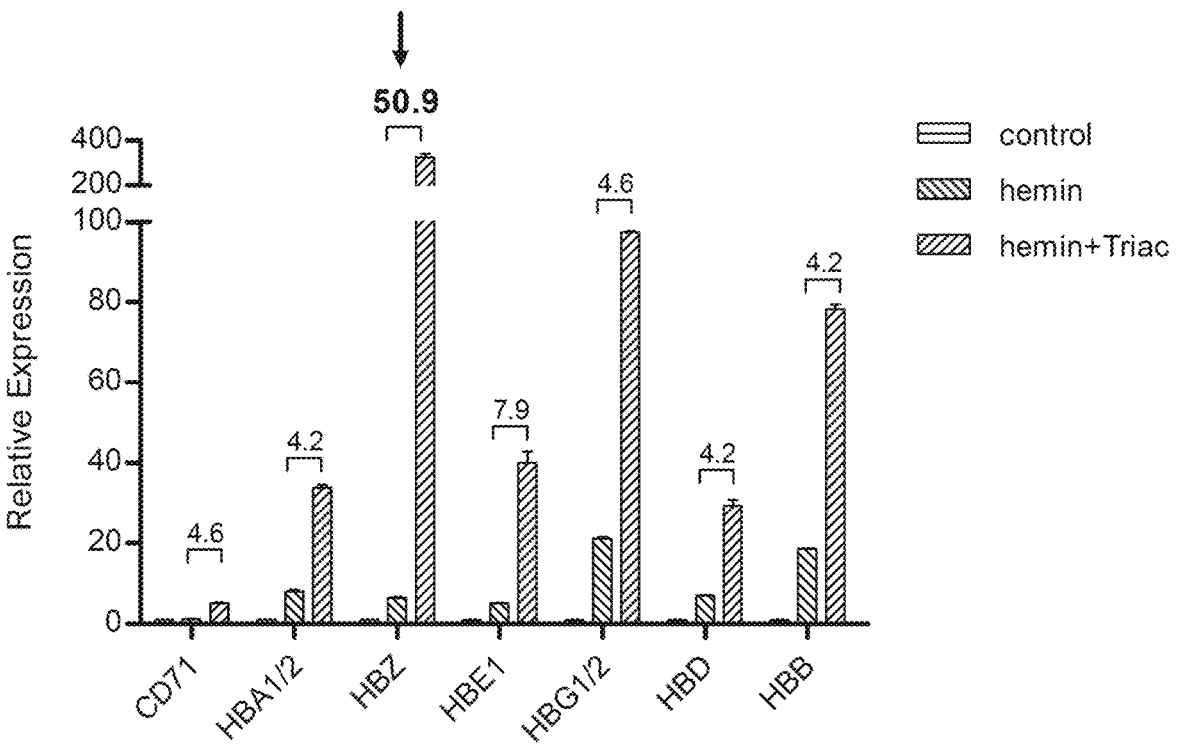
FIG. 1. The thyroid hormone analogue (Triac) induced ζ-globin gene (HBZ) expression in hemin-treated K562 cells.

As shown in FIG. 1, qPCR result shows that the expression of ζ-globin gene (HBZ) is up-regulated by 50.9 folds in Triac-treated K562 cells.

Actually, the human ζ-globin gene (HBZ) (NM 005332.3) sequence (SEQ ID NO.1) is as follows:

```
                                    (SEQ ID NO. 1)
    ATGTCTCTGACCAAGACTGAGAGGACCATCATTGT

GTCCATGTGGGCCAAGATCTCCACGCAGGCCGACA

CCATCGGCACCGAGACTCTGGAGAGGCTCTTCCTC

AGCCACCCGCAGACCAAGACCTACTTCCCGCACTT

CGACCTGCACCCGGGGTCCGCGCAGTTGCGCGCGC

ACGGCTCCAAGGTGGTGGCCGCCGTGGGCGACGCG

GTGAAGAGCATCGACGACATCGGCGGCGCCCTGTC

CAAGCTGAGCGAGCTGCACGCCTACATCCTGCGCG

TGGACCCGGTCAACTTCAAGCTCCTGTCCCACTGC

CTGCTGGTCACCCTGGCCGCGCGCTTCCCCGCCGA

CTTCACGGCCGAGGCCCACGCCGCCTGGGACAAGT

TCCTATCGGTCGTATCCTCTGTCCTGACCGAGAAG

TACCGCTGA.
```

Realtime PCR primers are as follows:

```
        Human-β-actin-F
                                    (SEQ ID NO. 2)
        CCAACCGCGAGAAGATGA Human-β-actin-R
                                    (SEQ ID NO. 3)
        CCAGAGGCGTACAGGGATAG Human-HBA1/2-F
                                    (SEQ ID NO. 4)
        AAGGTCGGCGCGCACGC
```

-continued

```
Human-HBA1/2-R
                                    (SEQ ID NO. 5)
CTCAGGTCGAAGTGCGGG Human-HBZ-F
                                    (SEQ ID NO. 6)
GGACCATCATTGTGTCCATGT Human-HBZ-R
                                    (SEQ ID NO. 7)
GGGAAGTAGGTCTTGGTCTGC Human-HBE1-F
                                    (SEQ ID NO. 8)
TGCATGTGGATCCTGAGAAC Human-HBE1-R
                                    (SEQ ID NO. 9)
CGACAGCAGACACCAGCTT Human-HBG1/2-F
                                    (SEQ ID NO. 10)
AGCACCTGGATGATCTCAAG Human-HBG1/2-R
                                    SEQ ID NO. 11)
AAACGGTCACCAGCACATTT( Human-HBD-F
                                    (SEQ ID NO. 12)
GATGCAGTTGGTGGTGAGG Human-HBD-R
                                    (SEQ ID NO. 13)
GGGTTGCCCATAACAGCAT Human-HBB-F
                                    (SEQ ID NO. 14)
GCACGTGGATCCTGAGAACT Human-HBB-R
                                    (SEQ ID NO. 15)
CACTGGTGGGGTGAATTCTT.
```

Embodiment 2

After treatment with Triac, T3 and T4 for 24 hours, respectively, zebrafish embryos were fixed by 4% paraformaldehyde. The expression of ζ-globin gene (hbae5) was detected by Whole-mount mRNA in situ hybridization (WISH).

Figure 2:
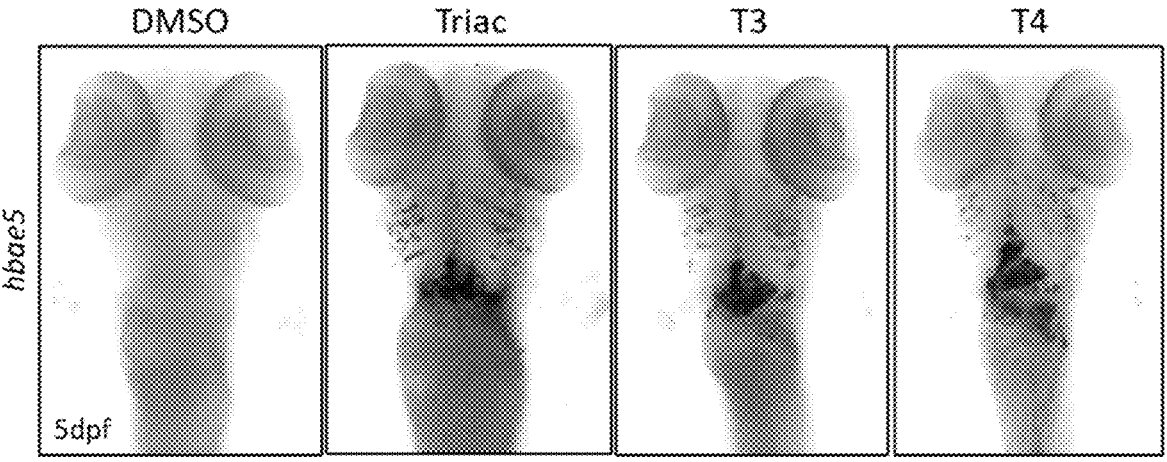
FIG. 2. WISH assay shows Triac, T3 or T4 induced ζ-globin gene (hbae5) expression in zebrafish embryos.

As shown in FIG. 2, Triac, T3 and T4 significantly induce the expression of ζ-globin gene (hbae5) in zebrafish embryos.

Embodiment 3

After treatment with Triac, T3 and T4 for 24 hours, respectively, zebrafish embryos were collected. TRIzol reagent (Invitrogen) was used to extract total RNA, then a reverse transcription kit (ReverTra Ace, TOYOBO) was used to synthesize cDNA, and finally, a SYBRGreen Real-time PCR Master Mix (TOYOBO) reagent was used to perform quantitative PCR.

The quantitative PCR reaction system is:

| | |
|---|---|
| 2 × SYBR Green PCR Master Mix | 5 ul |
| F-Primer(10 μmol/L) | 0.6 ul |

-continued

| | |
|---|---|
| R-Primer(10 μmol/L) | 0.6 ul |
| cDNA | 1 ul |
| ddH2O | 2.8 ul |
| Total volume | 10 ul |

The quantitative PCR reaction conditions are:

hot start: 95° C., 10 minutes;

denaturation: 95° C., 10 seconds; and annealing/extension: 60° C., 30 seconds.

40 circles.

Analysis of a Solubility Curve

Figure 3:
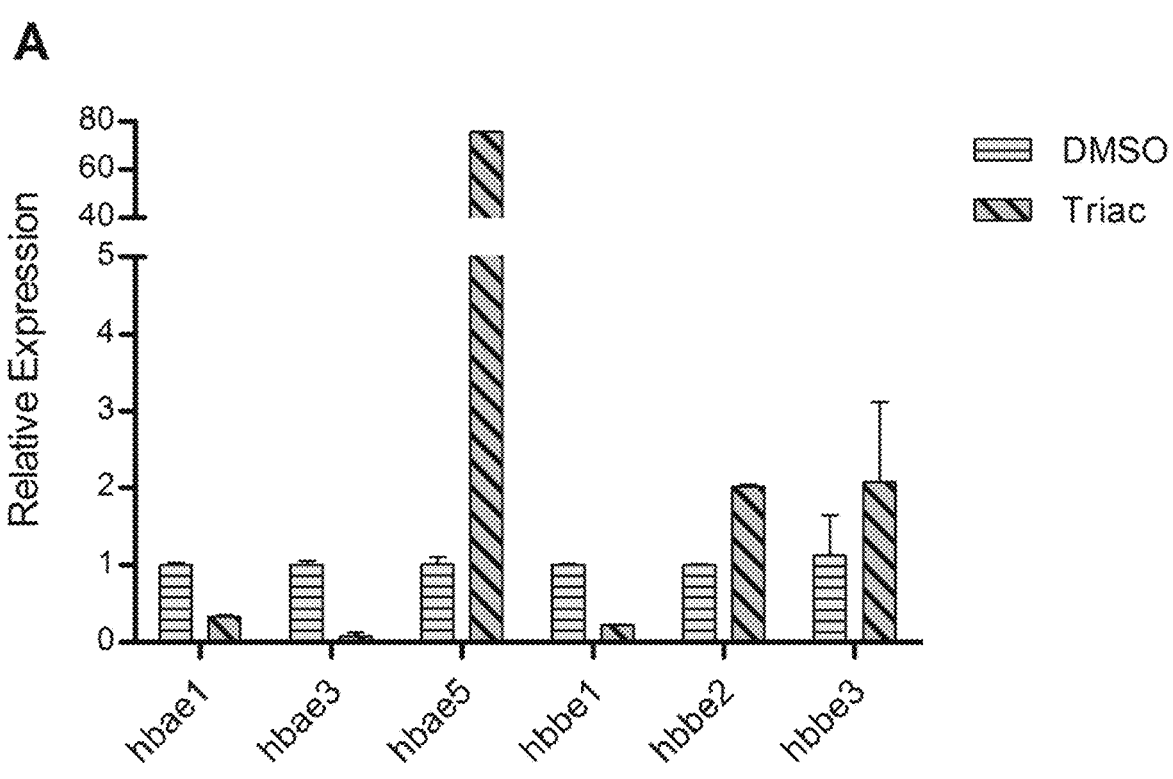
FIG. 3. qPCR shows Triac, T3 or T4 induced ζ-globin gene (hbae5) expression in zebrafish embryos.
Figure 3:
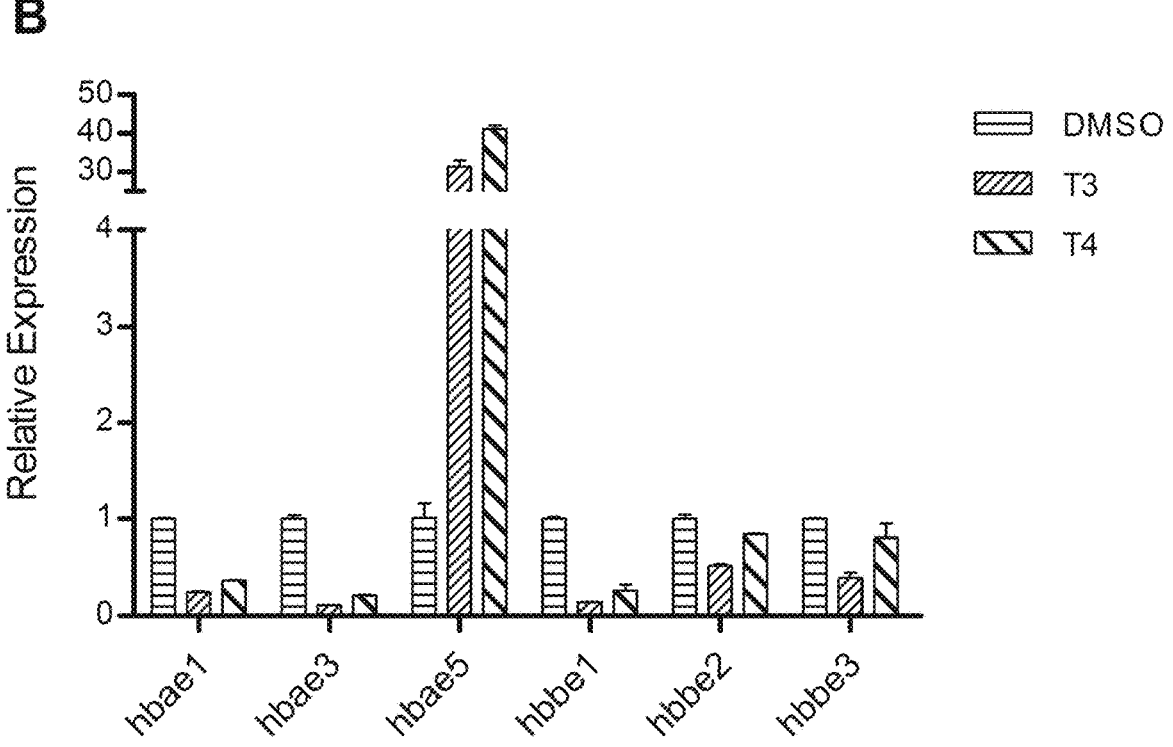

As shown in FIG. 3, qPCR result shows that the expression of ζ-globin gene (hbae5) is up-regulated by 76-folds, 31-folds and 41-folds in Triac, T3 and T4-treated zebrafish embryos, respectively.

Actually, the zebrafish ζ-globin gene (hbae5) (NM 001326701.1) sequence (SEQ ID NO.16) is as follows:

```
                                    (SEQ ID NO. 16)
ATGAGTCTTTCTGCTAAAGACAAGGCCGCCGTGAG

GGGCTTCTGGGCCAAGATTGCCCCAAAGGGAGAGC

AAATTGGTAACGAGGCGTTTTCCAGATTGCTTTTG

GTGTACCCTCAGACCAAGACCTACTTCTCCCACTG

GAACGATCTGGCCCCCGGCTCTCCCTCTGTGAAGA

AGCAGGGAAAGAAGATCGTCGGTGGACTCGGTCTG

GCTGTTGATAAAATCGACGACCTTTTCAACGGCCT

GCTGAACCTCAGTGAATTGCACGCCTTTCAGCTGA

GAGTCGACCCTGCTAACTTCAAGCTCCTGTCTCAC

TGTCTGCTGGTGGTGTTCGCCATGCTCTTCCCTGA

TGACTTCACCGCTGAGGTCCATCTGGCCATCGACA

AGTTCCTGGCAAGAGTGGCTTTGGCTCTGTCTGAC

AAATATCGTTAA.
```

Realtime PCR Primers are as Follows:

```
Zebrafish-β-actin-F
                                    (SEQ ID NO. 17)
TGCTGTTTTCCCCTCCATTG Zebrafish-β-actin-R
                                    (SEQ ID NO. 18)
TTCTGTCCCATGCCAACCA Zebrafish-hbae1-F
                                    (SEQ ID NO. 19)
CTGAGGCTGTCAGCAAAATCG Zebrafish-hbae1-R
                                    (SEQ ID NO. 20)
GAACAAAGTGGCCAGAACCAC Zebrafish-hbae3-F
                                    (SEQ ID NO. 21)
GCTGATGGATGACCTGAAGGG Zebrafish-hbae3-R
                                    (SEQ ID NO. 22)
CTCAGGAGTGAAGTCGTCTGG
```

-continued

Zebrafish-hbae5-F (SEQ ID NO. 23)

TGCTGAACCTCAGTGAATTGC

Zebrafish-hbae5-R (SEQ ID NO. 24)

GGAACTTGTCGATGGCCAGAT

Zebrafish-hbbe1-F (SEQ ID NO. 25)

TCCACGTAGATCCCGACAAC

Zebrafish-hbbe1-R (SEQ ID NO. 26)

TACTGTCTTCCCAGAGCGGA

Zebrafish-hbbe2-F (SEQ ID NO. 27)

GGACTGGACAGAGCCATGAAG

Zebrafish-hbbe2-R (SEQ ID NO. 28)

GAGGCAATCACGATTGTCAGG

-continued

Zebrafish-hbbe3-F (SEQ ID NO. 29)

TTGTGTGGACAGCTGAGGAG

Zebrafish-hbbe3-R (SEQ ID NO. 30)

ACGGATAGACGACCAAGCAT

The above description of the embodiments is for the purpose of allowing those of ordinary skill in the art to understand and use the present invention. Obviously, those skilled in the art may easily make various modifications on these embodiments, and may apply the general principles described herein to other embodiments without creative effort. Therefore, the present invention is not limited to the above embodiments. All improvements and modifications made by those skilled in the art according to the principle of the present invention without departing from the scope of the present invention should be within the protection scope of the present invention.

What is claimed is:

1. A method of treating sickle-cell disease, comprising administering Triac to a patient with the sickle-cell disease, wherein the Triac up-regulates expression of a ζ-globin gene, thereby inhibiting sickle hemoglobin polymerization.

* * * * *